United States Patent
Hsu et al.

(10) Patent No.: US 11,613,507 B2
(45) Date of Patent: Mar. 28, 2023

(54) METHOD FOR FABRICATING A HIGH-ACTIVITY DOUBLE-METAL-CYANIDE CATALYST

(71) Applicant: ORIENTAL UNION CHEMICAL CORP., Kaohsiung (TW)

(72) Inventors: Yu-Chuan Hsu, Kaohsiung (TW); Hsi-Chin Tsai, Kaohsiung (TW)

(73) Assignee: ORIENTAL UNION CHEMICAL CORP., Kaohsiung (TW)

( * ) Notice: Subject to any disclaimer, the term of this patent is extended or adjusted under 35 U.S.C. 154(b) by 178 days.

(21) Appl. No.: 17/150,456

(22) Filed: Jan. 15, 2021

(65) Prior Publication Data

US 2021/0130275 A1  May 6, 2021

Related U.S. Application Data

(60) Continuation of application No. 16/202,497, filed on Nov. 28, 2018, now abandoned, which is a division of application No. 15/847,344, filed on Dec. 19, 2017, now abandoned.

(51) Int. Cl.

| | |
|---|---|
| C07C 41/03 | (2006.01) |
| B01J 31/22 | (2006.01) |
| B01J 37/04 | (2006.01) |
| B01J 27/26 | (2006.01) |
| C08G 65/00 | (2006.01) |
| C08G 65/02 | (2006.01) |

(52) U.S. Cl.
CPC .............. *C07C 41/03* (2013.01); *B01J 27/26* (2013.01); *B01J 31/2208* (2013.01); *B01J 37/04* (2013.01); *C08G 65/00* (2013.01); *C08G 65/02* (2013.01); *B01J 2531/0202* (2013.01); *B01J 2531/26* (2013.01); *B01J 2531/845* (2013.01)

(58) Field of Classification Search
None
See application file for complete search history.

(56) References Cited

U.S. PATENT DOCUMENTS

| | | |
|---|---|---|
| 3,278,459 A | 10/1966 | Herold |
| 3,289,505 A | 12/1966 | Pyke |
| 3,427,256 A | 2/1969 | Milgrom |
| 3,829,505 A | 8/1974 | Herold |
| 4,477,589 A | 10/1984 | Van Der Hulst et al. |
| 5,158,922 A | 10/1992 | Hinney et al. |
| 5,470,813 A | 11/1995 | Le-Khac |
| 5,482,908 A | 1/1996 | Le-Khac |
| 5,545,601 A | 8/1996 | Le-Khac |
| 5,627,120 A | 5/1997 | Le-Khac |
| 2014/0163197 A1 * | 6/2014 | Quintanilla ........ C08G 65/2663 528/371 |

FOREIGN PATENT DOCUMENTS

WO    WO 01/04180   *   1/2001

* cited by examiner

*Primary Examiner* — Yun Qian

(74) *Attorney, Agent, or Firm* — Muncy, Geissler, Olds & Lowe, P.C.

(57) ABSTRACT

A high-activity double-metal-cyanide catalyst, a method for fabricating the same, and applications of the same are disclosed. An organic complexing ligand, which is formed via mixing fatty alcohols and alicyclic carbonates, is used to generate a high-activity double-metal-cyanide catalyst. The high-activity double-metal-cyanide catalyst includes at least one double-metal-cyanide compound, at least one organic complexing ligand, and an optional functionalized compound. The double-metal-cyanide catalyst of the present invention has a higher activity than the conventional double-metal-cyanide catalysts. The polyols generated by the present invention has an insignificant amount of high-molecular-weight compounds.

12 Claims, 4 Drawing Sheets

METHOD FOR FABRICATING A HIGH-ACTIVITY DOUBLE-METAL-CYANIDE CATALYST

CROSS-REFERENCE TO RELATED APPLICATIONS

This application is a Continuation-in-Part of co-pending application Ser. No. 16/202,497, filed on Nov. 28, 2018, which is a Divisional of co-pending application Ser. No. 15/847,344 filed on Dec. 19, 2017, for which priority is claimed under 35 U.S.C. § 120, the entire contents of which are hereby incorporated by reference.

BACKGROUND OF THE INVENTION

Field of the Invention

The present invention relates to a high-activity double-metal-cyanide (DMC) catalyst, particularly to a technology using an alicyclic carbonate as the constituent of the organic complexing ligand to enhance the activity of a DMC catalyst and using the high-activity DMC catalyst to produce polyols containing an insignificant amount of high-molecular-weight components.

Description of the Related Art

The double-metal-cyanide (DMC) catalyst can function as a superior catalyzing agent of the polymerization of epoxides. The DMC catalyst has high activity. The polyols fabricated with the DMC catalyst has a lower unsaturation level than that fabricated with the potassium hydroxide (KOH) catalyst. The DMC catalyst may be used to fabricate polyether polyols, polyester polyols, polyether-ester polyols, which are mostly applied to polyurethane coatings, elastomers, sealants, foams and adhesives.

The typical methods of fabricating DMC are using an aqueous solution reaction of metal salts and metal cyanide salts to form deposition of DMC, such as the methods disclosed in U.S. Pat. Nos. 3,427,256, 3,289,505 and 5,158,922. Some improved DMC fabrication methods use organic complexing ligands to make DMC having appropriate activity, such as the methods disclosed in U.S. Pat. Nos. 3,278,459, 3,829,505, 4,477,589 and 5,470,813. Some DMC fabrication methods add functionalized polymers to further enhance the activity of DMC, such as the methods disclosed in U.S. Pat. Nos. 5,482,908, 5,545,601 and 5,627,120. In comparison with the KOH-based methods, the DMC-based methods have advantages of high reaction speed and low unsaturation level. However, the polyols fabricated by the DMC-based methods contain more high-molecular-weight compounds, such as the compounds having an average molecular weight higher than 400000. The high-molecular-weight compounds will reduce the workability after the polyols are processed. For example, after processing, the polyols become tight foam, or the foam thereof is easy to settle or collapse. Many methods were proposed to overcome the abovementioned problems, such as redesigning the formula of polyurethane or removing high-molecular-weight compounds from polyols. However, these methods are too expensive to apply industrially.

SUMMARY OF THE INVENTION

The primary objective of the present invention is to provide a high-activity double-metal-cyanide (DMC) catalyst, a method for fabricating the same, and applications of the same. The present invention uses an alicyclic carbonate as the constituent of the organic complexing ligand to fabricate a high-activity DMC catalyst. In addition to increasing the activity of the DMC catalyst, the present invention also decrease the amount of high-molecular-weight compounds in polyols.

In order to achieve the abovementioned objective, the present invention proposes a high-activity double-metal-cyanide (DMC) catalyst, which comprises at least one double-metal-cyanide compound and at least one organic complexing ligand, wherein the organic complexing ligand is a mixture of a C2-C7 fatty alcohol and an alicyclic carbonate, and wherein the concentration of the fatty alcohol in the organic complexing ligand is 2-98 mole %. The alicyclic carbonate of the organic complexing ligand has a structural formula expressed by chemical formula (I):

wherein R and R' may be the same or different, and wherein each of R and R' is selected from a group consisting of hydrogen atoms, saturated alkyl groups each containing 1-20 carbon atoms, cyclic alkyl groups, hydroxyl groups, and vinyl groups.

The double metal cyanide of the abovementioned high-activity double-metal-cyanide catalyst is the product of the reaction of at least one metal salt and at least one metal cyanide salt.

The metal salt has a general formula expressed by chemical formula (II):

wherein M in chemical formula (II) is selected from a group consisting of bivalent zinc (Zn(II)), bivalent iron (Fe (II)), bivalent nickel (Ni (II)), bivalent manganese (Mn (II)), bivalent cobalt (Co (II)), bivalent tin (Sn (II)), bivalent lead (Pb (II)), trivalent iron (Fe (III)), tetravalent molybdenum (Mo (IV)), hexavalent molybdenum (Mo (VI)), trivalent aluminum (Al (III)), pentavalent vanadium (V (V)), tetravalent vanadium (V (IV)), bivalent strontium (Sr (II)), tetravalent tungsten (W (IV)), hexavalent tungsten (W (VI)), bivalent copper (Cu (II)), and trivalent chromium (Cr (III)), and wherein X is selected from a group consisting of halogens, hydroxyl ion, sulfate ion, carbonate ion, cyanide ion, isocyanide ion, isothiocyanate ion, carboxylate ion, and nitrate ion, and wherein n equals 1-3 and the charges in chemical formula (II) are in balance.

The metal cyanide salt has a general formula expressed by chemical formula (III):

wherein M in chemical formula (III) is selected from a group consisting of bivalent iron (Fe (II)), trivalent iron (Fe (III)), bivalent cobalt (Co (II)), trivalent cobalt (Co (III)), bivalent chromium (Cr (II)), trivalent chromium (Cr (III)), bivalent manganese (Mn (II)), trivalent manganese (Mn (III)), trivalent iridium (Ir (III)), bivalent nickel (Ni (II)), trivalent rhodium (Rh (III)), bivalent ruthenium (Ru (II)), tetravalent vanadium (V (IV)), and pentavalent vanadium (V (V)), and wherein M' is selected from a group consisting of alkali metal ions and alkaline earth metal ions, and wherein A is an anion which is selected from a group consisting of halides, hydroxyl ion, sulfate ion, carbonate ion, cyanide ion, oxalate ion, thiocyanate isocyanide ion, isothiocyanate ion, carboxylate ion, and nitrate ion, and wherein each of a and b is an integer greater than 1, and wherein the sum of the charges of the groups subscripted by a, b and c is equal to the number of the charges of M.

In the abovementioned high-activity DMC catalyst, the fatty alcohol is one or more compounds selected from a group consisting of ethanol, n-propyl alcohol, isopropyl alcohol, n-butanol, isobutyl alcohol, sec-butyl alcohol, tert-butyl alcohol, 2-methyl-3-buten-2-ol, and tert-amyl alcohol.

In the abovementioned high-activity DMC catalyst, the alicyclic carbonate is selected from a group consisting of ethylene carbonate, propylene carbonate, 1,2-butylene carbonate, pentylene carbonate, hexylene carbonate, octylene carbonate, dodecylene carbonate, glycerol carbonate, styrene carbonate, 3-phenyl propylene carbonate, cyclohexene carbonate, vinyl ethylene carbonate, 4, 4-dimethyl-5-methylene-(1, 3) dioxolan-2-one, 4-allyl-4, 5-dimethyl-5-(10-undecenyl)-1, 3-dioxolan-2-one.

The abovementioned high-activity DMC catalyst may further comprise at least one functionalized compound or a water-soluble salt of the functionalized compound. The concentration of the functionalized compound or the water-soluble salt thereof in the high-activity DMC catalyst is 2-80 wt %. The functionalized compound is defined to be a compound containing at least one functional group. The functional group may be selected from a group consisting of oxygen, nitrogen, sulfur, phosphorus, and halogens.

The present invention also proposes a method for fabricating the high-activity DMC catalyst, wherein two metal precursor solutions are mixed to react in the presence of the abovementioned organic complexing ligand, and wherein at least one of the metal precursor solutions contains a cyanide ligand. After the reaction, the solution is flushed and filtered repeatedly to remove the salts and separate the high-activity DMC catalyst from the solution.

In one embodiment, the organic complexing ligand exists in at least one of the metal precursor solutions and fully mixes with the metal precursor. Alternatively, the organic complexing ligand is added to the solution immediately after two metal precursor solutions are mixed.

In one embodiment, a functionalized compound or the water-soluble salt of the functionalized compound is selectively added to the metal precursor solution and/or the organic complexing ligand.

The present invention also proposes a method for fabricating polyols, wherein the high-activity DMC catalyst is used to enable a polyaddition reaction of at least one alkylene oxide and at least one starter compound containing active hydrogen atoms, whereby to generate the polyols.

In one embodiment, the abovementioned polyaddition reaction is undertaken at a temperature of 25-200° C. and a pressure of 0.0001-20 bar.

In one embodiment, the concentration of the high-activity DMC catalyst in the polyaddition reaction is 0.0005-1 wt %.

Compared with the conventional DMC catalysts, the DMC catalyst of the present invention has higher activity and favors generating polyols having an insignificant amount of high-molecular-weight compounds.

Below, embodiments are described in detail to make easily understood the objectives, technical contents, characteristics and accomplishments of the present invention.

DETAILED DESCRIPTION OF THE INVENTION

Figure 1:
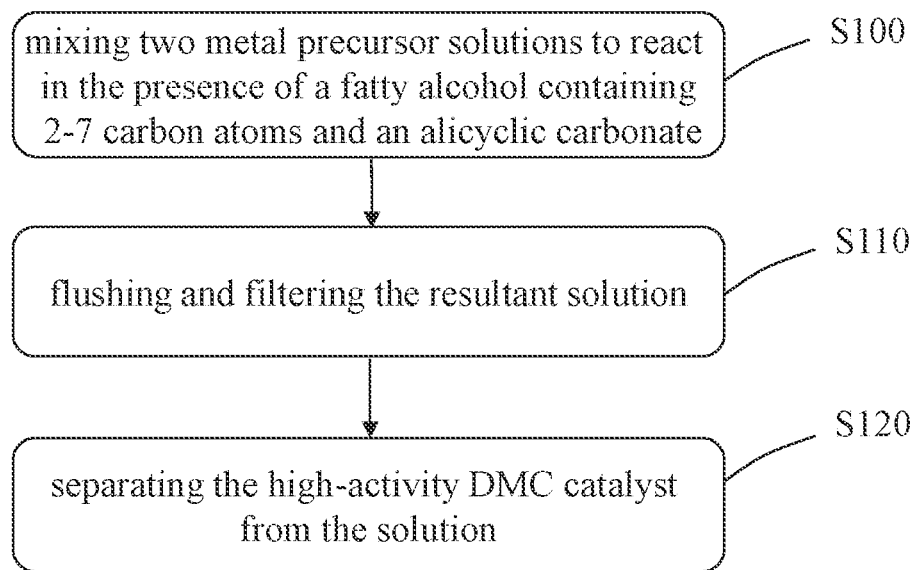
FIG. 1 is a flowchart of a method for fabricating a high-activity DMC catalyst according to one embodiment of the present invention.

The present invention discloses a high-activity double-metal-cyanide (DMC) catalyst, which comprises at least one double-metal-cyanide compound and at least one organic complexing ligand, wherein the organic complexing ligand is a mixture of a C2-C7 fatty alcohol and an alicyclic carbonate, and wherein the concentration of the fatty alcohol in the organic complexing ligand is 2-98 mole %. The alicyclic carbonate of the organic complexing ligand has a structural formula expressed by chemical formula (I):

(I)

wherein R and R' may be the same or different, and wherein each of R and R' is selected from a group consisting of hydrogen atoms, saturated alkyl groups each containing 1-20 carbon atoms, cyclic alkyl groups, hydroxyl groups, and vinyl groups.

The double metal cyanide of the abovementioned high-activity double-metal-cyanide catalyst is the product of the reaction of at least one metal salt and at least one metal cyanide salt.

The metal salt has a general formula expressed by chemical formula (II):

$M(X)_n$ (II)

In chemical formula (II), M may be but is not limited to be selected from a group consisting of bivalent zinc (Zn(II)), bivalent iron (Fe (II)), bivalent nickel (Ni (II)), bivalent manganese (Mn (II)), bivalent cobalt (Co (II)), bivalent tin (Sn (II)), bivalent lead (Pb (II)), trivalent iron (Fe (III)), tetravalent molybdenum (Mo (IV)), hexavalent molybdenum (Mo (VI)), trivalent aluminum (Al (III)), pentavalent vanadium (V (V)), tetravalent vanadium (V (IV)), bivalent strontium (Sr (II)), tetravalent tungsten (W (IV)), hexavalent tungsten (W (VI)), bivalent copper (Cu (II)), and trivalent chromium (Cr (III)), and In chemical formula (II), X is an anion, which may be but is not limited to be selected from a group consisting of halogens, hydroxyl ion, sulfate ion, carbonate ion, cyanide ion, isocyanide ion, isothiocyanate ion, carboxylate ion, and nitrate ion.

In chemical formula (II), n equals 1-3, and the charges in chemical formula (II) are in balance.

Specifically, the metal salt may be but is not limited to be selected from a group consisting of zinc chloride, zinc sulfate, zinc bromide, zinc formate, zinc acetate, zinc propionate, zinc acetonylacetate, zinc benzoate, zinc nitrate, iron (II) sulfate, iron (II) bromide, cobalt (II) chloride, cobalt (II) thiocyanate, nickel (II) formate, nickel (II) nitrate, and the likes. The abovementioned metal salts may be used singly or jointly. Preferably, zinc halides are used as the metal salts.

The metal cyanide salt used by the present invention has a general formula expressed by chemical formula (III):

$$(M')_a M(CN)_b (A)_c \quad (III)$$

In chemical formula (III), M may be but is not limited to be selected from a group consisting of bivalent iron (Fe (II)), trivalent iron (Fe (III)), bivalent cobalt (Co (II)), trivalent cobalt (Co (III)), bivalent chromium (Cr (II)), trivalent chromium (Cr (III)), bivalent manganese (Mn (II)), trivalent manganese (Mn (III)), trivalent iridium (Ir (III)), bivalent nickel (Ni (II)), trivalent rhodium (Rh (III)), bivalent ruthenium (Ru (II)), tetravalent vanadium (V (IV)), and pentavalent vanadium (V (V)). It is preferred: M is selected from a group consisting of bivalent cobalt (Co (II)), trivalent cobalt (Co (III)), bivalent iron (Fe (II)), trivalent iron (Fe (III)), trivalent chromium (Cr (III)), trivalent iridium (Ir (III)), and bivalent nickel (Ni (II)). The abovementioned metals may be singly or jointly used as the metal of the metal cyanide salt.

In chemical formula (III), M' is selected from a group consisting of alkali metal ions and alkaline earth metal ions.

In chemical formula (III), A is an anion, which may be but is not limited to be selected from a group consisting of halides, hydroxyl ion, sulfate ion, carbonate ion, cyanide ion, oxalate ion, thiocyanate isocyanide ion, isothiocyanate ion, carboxylate ion, and nitrate ion.

In chemical formula (III), each of a and b is an integer greater than 1, and the sum of the charges of the groups subscripted by a, b and c is equal to the number of the charges of M.

Specifically, the metal cyanide salt is selected from a group consisting of potassium hexacyanocobaltate (III), potassium hexacyanoferrate (II), potassium hexacyanoferrate (III), lithium hexacyanoiridate (III), lithium hexacyanocobaltate (III), sodium hexacyanocobaltate (III), calcium hexacyanocobaltate (III), cesium hexacyanocobaltate (III) and the likes. The abovementioned metal cyanide salts may be used singly or jointly. Preferably, metal hexacyanocobaltate salts are used as the metal cyanide salts.

The double-metal-cyanide compound used by the present invention may be but is not limited to be selected from a group consisting of zinc hexacyanocobaltate(III), zinc hexacyanoferrate (II), zinc hexacyanoferrate (III), nickel (II) hexacyanoferrate (II), cobalt (II) hexacyanocobaltate (III), and the likes. For other examples of the double-metal-cyanide compounds, please refer to the U.S. Pat. No. 5,158,922. Preferably, zinc hexacyanocobaltate (III) is used as the double-metal-cyanide compound.

The organic complexing ligand used by the present invention is a mixture of a C2-C7 fatty alcohol and an alicyclic carbonate. Specifically, the fatty alcohol is selected from a group consisting of ethanol, n-propyl alcohol, isopropyl alcohol, n-butanol, isobutyl alcohol, sec-butyl alcohol, tert-butyl alcohol, 2-methyl-3-buten-2-ol, tert-amyl alcohol, and the likes. The abovementioned fatty alcohols may be singly or jointly used. Preferably, the branched alcohols are used as the fatty alcohols, especially tert-butyl alcohol and 2-methyl-3-buten-2-ol.

Specifically, the alicyclic carbonate is selected from a group consisting of ethylene carbonate, propylene carbonate, 1,2-butylene carbonate, pentylene carbonate, hexylene carbonate, octylene carbonate, dodecylene carbonate, glycerol carbonate, styrene carbonate, 3-phenyl propylene carbonate, cyclohexene carbonate, vinyl ethylene carbonate, 4, 4-dimethyl-5-methylene-(1, 3) dioxolan-2-one, 4-allyl-4, 5-dimethyl-5-(10-undecenyl)-1, 3-dioxolan-2-one, and the likes.

The organic complexing ligand used by the present invention, which is formed via mixing a fatty alcohol and an alicyclic carbonate, can enhance the activity of the DMC catalyst and decrease the amount of high-molecular-weight compounds (whose average molecular weight is greater than 400000) in the produced polyols. If an organic complexing ligand does not contain any alicyclic carbonate but only contains fatty alcohol, the organic complexing ligand can also enhance the activity of the DMC catalyst, such as the technology disclosed by the U.S. Pat. No. 5,470,813. However, the polyol produced by the conventional technology has too high an amount of high-molecular-weight (greater than 400000 in average) compounds in the produced polyol to meet expectation. If an organic complexing ligand does not contain any fatty alcohol but only contains alicyclic carbonate, the activity of the DMC catalyst would be significantly decreased. Besides, the range of the distribution of the molecular weights of the product is broadened, and the viscosity thereof is increased.

The present invention may modify the proportions of the fatty alcohol and the alicyclic carbonate in the organic complexing ligand to adjust the activity of the DMC catalyst, the viscosity of the polyol, and the like properties. The range of the concentration of the alicyclic carbonate in the organic complexing ligand is preferably 2-98 mole %, more preferably 5-95 mole %, most preferably 10-50 mole %.

The high-activity DMC catalyst disclosed by the present invention can optionally contain at least one functionalized compound or the water-soluble salt thereof. The functionalized compound is defined to be a compound having one or more functional groups. The functional group may be but is not limited to be selected from a group consisting of oxygen, nitrogen, sulfur, phosphorus, and halogens. Specifically, the functionalized compound is selected from a group consisting of polyethers, polyesters, polycarbonates, polyalkylene glycol sorbitan esters, polyalkylene glycol glycidyl ethers, polyacrylamides, poly(acrylamide-co-acrylic acids), polyacrylic acids, poly(acrylic acid-co-maleic acid), poly(N-vinylpyrrolidone-co-acrylic acids), poly(acrylic acid-co-styrenes), salts of poly(acrylic acid-co-styrenes), maleic acids, styrenes and maleic anhydride copolymers, salts of styrenes and maleic anhydride copolymers, polyacrylonitriles, polyalkyl acrylates, polyalkyl methacrylates, polyvinyl methyl ethers, polyvinyl ethyl ethers, polyvinyl acetates, polyvinyl alcohols, poly-N-vinylpyrrolidones, polyvinyl methyl ketones, poly(4-vinylphenols), oxazoline polymers, polyalkyleneimines, hydroxyethylcelluloses, polyacetals, glycidyl ethers, glycosides, carboxylic acid esters of polyhydric alcohols, bile acids, salts, esters and amides of bile acids, cyclodextrins, phosphorus compounds, unsaturated carboxylic acid ester, and ionic surface- or interface-active compounds. The functionalized compound is preferably selected from polyethers. Please also refer to the U.S. Pat. No. 5,714,428 for other compounds suitable for the functionalized compound of the present invention.

The solubility of the functionalized compound or the salt thereof to water or the solvent miscible with water is at least 3 wt %. Specifically, the solvent miscible with water is tetrahydrofuran, acetone, acetonitrile, tert-butyl alcohol, or the like. The solubility of the functionalized compound or the salt thereof to water is very important, determining whether the functionalized compound or the salt thereof can combine with double metal cyanide while double metal cyanide is formed and precipitated.

The concentration of the functionalized compound or the water-soluble salt thereof in the DMC catalyst is preferably 2-80 wt %, more preferably 5-70 wt %, most preferably 10-60 wt %.

Refer to FIG. 1 a flowchart of a method for fabricating a high-activity DMC catalyst according to one embodiment of the present invention.

In Step S100, mix two metal precursor solutions to react in the presence of the abovementioned fatty alcohol containing 2-7 carbon atoms and the abovementioned alicyclic carbonate to generate a resultant solution, wherein at least one of the metal precursor solutions contains a cyanide ligand. The resultant solution contains a double-metal-cyanide compound and an organic complexing ligand including the fatty alcohol and the alicyclic carbonate, wherein the alicyclic carbonate coordinates with the double-metal-cyanide compound, wherein a concentration of the fatty alcohol in the organic complexing ligand is 2-98 mole %, and wherein the alicyclic carbonate has a structural formula expressed by above-mentioned chemical formula (I). In one embodiment, the fatty alcohol and the alicyclic carbonate exist in at least one of the metal precursor solutions and fully mix with the metal precursor; then the two metal precursor solutions are mixed. In one embodiment, none of the two metal precursor solutions has the fatty alcohol and the alicyclic carbonate; the fatty alcohol and the alicyclic carbonate are added to the solution immediately after two metal precursor solutions are mixed; then precipitation is generated. In one embodiment, at least one functionalized compound or the water-soluble salt thereof is added to the metal precursor solutions and/or the organic complexing ligand.

The combination of the abovementioned reactants may be achieved via any suitable mixing method, such as a simple mixing method, a high-shear mixing method, a homogenization method, etc. Preferably, the homogenization method or the high-shear mixing method is used to mix the reactants.

In the method for fabricating a high-activity DMC catalyst of the present invention, the metal precursor solutions are preferably mixed in an aqueous solution at a temperature of 10-80° C.

Next, the process proceeds to Step S110. In Step S110, repeat flushing and filtering the resultant solution of the reaction to remove salts from the solution and remove the excess organic complexing ligand from the resultant solution to make free alicyclic carbonate be absent.

The high-activity DMC catalyst generated in the resultant solution can be separated from the liquid using a known technology, such as centrifugation, filtration, pressurized filtration, decanting, phase separation, or aqueous separation.

The aqueous solution of fatty alcohol, which is generated via mixing water and fatty alcohol, may be used to flush the high-activity DMC catalyst generated in the resultant solution. In one embodiment, the aqueous fatty alcohol solution contains at least one functionalized compound or a mixture or compound of at least two functionalized compounds. After the high-activity DMC catalyst has been flushed and separated from the solution, an aqueous fatty alcohol solution or an alcohol-containing aqueous solution is further used to flush the high-activity DMC catalyst, wherein the aqueous fatty alcohol solution or the alcohol-containing aqueous solution has at least one functionalized compound or a mixture or compound of at least two functionalized compounds. A water-free solution is preferably used in the final flushing step of the high-activity DMC catalyst.

In Step S120, separate the high-activity DMC catalyst without free alicyclic carbonate from the resultant solution.

The primary objective of the present invention is to provide a high-activity DMC catalyst. When synthesizing the high-activity DMC catalyst, the alicyclic carbonate and the fatty alcohol play the role of the organic complexing ligand together in order to enhance the activity of the high-activity DMC catalyst. The alicyclic carbonate is only combined with a metal ion from the double-metal-cyanide compound, and no free alicyclic carbonate will enter any subsequent reaction systems using the high-activity DMC as a catalyst.

Figure 2:
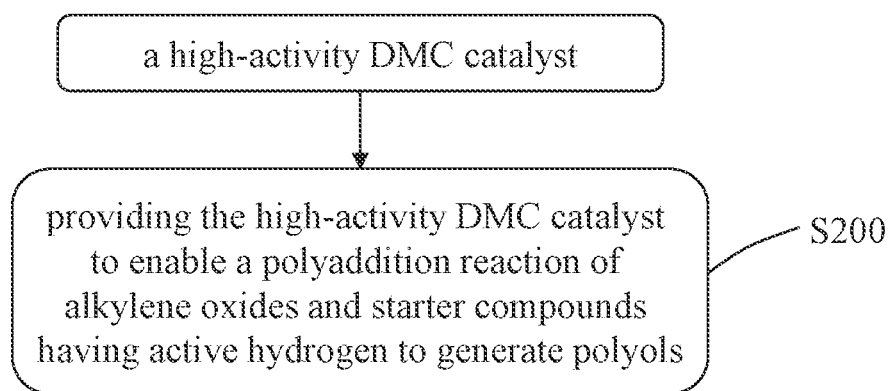
FIG. 2 is a flowchart of a method for fabricating polyols according to one embodiment of the present invention.

The present invention further discloses a method for fabricating polyols, especially polyether polyols. Refer to FIG. 2 a flowchart of a method for using a high-activity DMC catalyst to fabricate polyols according to one embodiment of the present invention.

In Step S200, use the high-activity DMC catalyst of the present invention to catalyze a polyaddition reaction of one or more kinds of alkylene oxides and one or more kinds of starter compounds having active hydrogen to generate polyols. The high-activity double-metal-cyanide catalyst without free alicyclic carbonate makes free alicyclic carbonate be absent in the polyaddition reaction.

The alkylene oxide preferably used by the present invention may be but is not to be selected from a group consisting of ethylene oxide, propylene oxide, butylene oxide, and the mixtures thereof. The polyether chain of any kind of polyol can be formed via alkoxylating the monomers of a single kind of alkylene oxide, the monomers of 2-3 kinds of alkylene oxides arranged arbitrarily, or the monomers of 2-3 kinds of alkylene oxides arranged blockwise.

The starter compound having active hydrogen used by the present invention may be but is not limited to be a compound containing 1-8 hydroxyl groups and having a weight average molecular weight (M) of 18-2000, preferably 32-2000. Specifically, the starter compound having active hydrogen is selected from a group consisting of polyoxypropylene polyols, polyoxyethylene polyols, poly(tetramethylene ether) glycols, glycerol, propoxylated glycerols, propylene glycol, tripropylene glycol, alkoxylated allylic alcohols, bisphenol A, pentaerythritol, sorbitol, sucrose, degraded starch, Mannich polyols, water, and combinations thereof.

The starter compound having active hydrogen used by the present invention may be alkoxylated with any known method, which may be but is not limited to be a batch-type process, a semi-batch type process or a continuous type process. The alkoxylation is undertaken at a temperature of 25-200° C., preferably 50-180° C., most preferably 60-150° C. The alkoxylation is undertaken at a pressure of 0.0001-20 bar. In alkoxylation, the amount of the added high-activity DMC catalyst should be appropriately controlled to make the reaction fully controllable under the provided reaction conditions. The concentration of the high-activity DMC catalyst in an ordinary reaction is preferably 0.0005-1 wt %, more preferably 0.001-0.1 wt %, most preferably 0.001-0.005 wt %.

The polyol fabricated by the present invention contains 1-8 hydroxyl groups, preferably 2-6 hydroxyl groups, most preferably 2-4 hydroxyl groups. The ratio of the alkylene oxide to the starter compound having active hydrogen correlates with the target molecular weight of the polyols. The higher the ratio, the larger the molecular weight of the polyol. In general, the range of the weight average molecular weights of the polyols is 500-100000 g/mole, preferably 1000-20000 g/mole, most preferably 2000-16000 g/mole.

While the high-activity DMC catalyst of the present invention is used in fabricating polyols, the amount of high-molecular-weight (greater than 400000 in average) compounds is decreased. Besides, the high-activity DMC catalyst of the present invention has higher reactivity than the DMC catalysts disclosed in the conventional technologies. The high-molecular-weight (greater than 400000 in average) compounds can be quantitatively measured in any appropriate method. The present invention uses a gel permeation chromatography (GPC) method. The GPC equipment is provided by Waters Cooperation Taiwan, including the analyzer ACQUITY APC System and the detector ACQUITY ELSD. The column assembly thereof includes ACQUITY APC XT 45 Å, 1.7 μm, 4.6 mm×150 mm, ACQUITY APC XT 125 Å, 2.5 μm, 4.6 mm×150 mm, and ACQUITY APC XT 200 Å, 2.5 μm, 4.6 mm×150 mm, which are connected in series. In the analysis of the high-molecular-weight compounds in polyols, the polystyrene having molecular weights of 20000-1000000 is used to produce the calibration curve; the limit of the quantitative analysis is 5 ppm; the range of detected molecular weights is 1000-2000000.

Below, several embodiments are provided to further demonstrate how to fabricate the high-activity DMC catalyst of the present invention, how to use the catalyst of the present invention to catalyze the polyaddition reaction of alkylene oxides and starter compounds having active hydrogen to generate polyols.

Embodiment I

Use ethylene carbonate (EC) and tert-butyl alcohol (TBA) as the organic complexing ligand to fabricate the high-activity DMC catalyst:

Mix 94 g zinc chloride ($ZnCl_2$), 33 g ethylene carbonate (EC), 176 g tert-butyl alcohol (TBA), and 1375 g water to form Solution A; mix 38 g potassium hexacyanocobaltate (III) ($K_3Co(CN)_6$), 13 g ethylene carbonate (EC), 71 g tert-butyl alcohol (TBA), and 500 g water to form Solution B; mix Solution A and Solution B and agitate them uniformly at an ambient temperature to generate a white solid in the solution; use pressurized filtration to separate the solid from the solution; add the solid to a mixture solution of 508 g tert-butyl alcohol (TBA) and 275 g water, and agitate them at an ambient temperature to disperse the solid uniformly in the solution; use pressurized filtration to separate the solid from the solution; add the solid to 723 g tert-butyl alcohol (TBA) and agitate them at an ambient temperature to disperse the solid uniformly in the solution; use pressurized filtration to separate the solid from the solution; dry the solid in vacuum at a temperature of 60° C. to obtain the high-activity DMC catalyst.

Embodiment II

Use ethylene carbonate (EC) and tert-butyl alcohol (TBA) as the organic complexing ligand to fabricate the high-activity DMC catalyst:

Embodiment II is the same as Embodiment I except the changes stated below: ethylene carbonate (EC) is changed to be 51 g and tert-butyl alcohol (TBA) is changed to be 159 g in Solution A; ethylene carbonate (EC) is changed to be 20 g and tert-butyl alcohol (TBA) is changed to be 64 g in Solution B.

Embodiment III

Use ethylene carbonate (EC) and tert-butyl alcohol (TBA) as the organic complexing ligand and add polypropylene glycol (PPG) to fabricate the high-activity DMC catalyst:

Mix 94 g zinc chloride ($ZnCl_2$), 33 g ethylene carbonate (EC), 176 g tert-butyl alcohol (TBA), and 1375 g water to form Solution A; mix 38 g potassium hexacyanocobaltate (III) ($K_3Co(CN)_6$), 13 g ethylene carbonate (EC), 71 g tert-butyl alcohol (TBA), and 500 g water to form Solution B; mix 40 g polypropylene glycol (PPG) having a molecular weight of 400, 9 g tetrahydrofuran (THF), and 500 g water to form Solution C; mix Solution A and Solution B and agitate them uniformly at an ambient temperature to form a mixture solution; add Solution C to the mixture solution of Solution A and Solution B and agitate them for 3 minutes; use pressurized filtration to separate a solid from the solution; add the solid to a mixture solution containing 10 g polypropylene glycol (PPG) having a molecular weight of 400, 9 g tetrahydrofuran (THF), 508 g tert-butyl alcohol (TBA), and 275 g water, and agitate them at an ambient temperature to disperse the solid uniformly in the solution; use pressurized filtration to separate the solid from the solution; add the solid to a mixture solution containing 5 g polypropylene glycol (PPG) having a molecular weight of 400, 9 g tetrahydrofuran (THF), and 723 g tert-butyl alcohol (TBA), and agitate them at an ambient temperature to disperse the solid uniformly in the solution; use pressurized filtration to separate the solid from the solution; dry the solid in vacuum at a temperature of 60° C. to obtain the high-activity DMC catalyst.

Comparison I

Use Tert-Butyl Alcohol (TBA) as the Organic Complexing Ligand to Fabricate the High-Activity DMC Catalyst:

Mix 100 g zinc chloride ($ZnCl_2$), 388 g tert-butyl alcohol (TBA), and 1000 g water to form Solution A; mix 40 g potassium hexacyanocobaltate (III) ($K_3Co(CN)_6$) and 400 g water to form Solution B; mix Solution A and Solution B and agitate them uniformly at an ambient temperature to generate a white solid in the solution; use pressurized filtration to separate the solid from the solution; add the solid to a mixture solution of 680 g tert-butyl alcohol (TBA) and 375 g water, and agitate them at an ambient temperature to disperse the solid uniformly in the solution; use pressurized filtration to separate the solid from the solution; add the solid to 970 g tert-butyl alcohol (TBA) and agitate them at an ambient temperature to disperse the solid uniformly in the solution; use pressurized filtration to separate the solid from the solution; dry the solid in vacuum at a temperature of 60° C. to obtain the high-activity DMC catalyst.

Comparison II

Use Tert-Butyl Alcohol (TBA) as the Organic Complexing Ligand and Add Polypropylene Glycol (PPG) to Fabricate the High-Activity DMC Catalyst:

Mix 100 g zinc chloride ($ZnCl_2$), 388 g tert-butyl alcohol (TBA), and 750 g water to form Solution A; mix 40 g potassium hexacyanocobaltate (III) ($K_3Co(CN)_6$) and 400 g water to form Solution B; mix 40 g polypropylene glycol (PPG) having a molecular weight of 400, 8 g tert-butyl alcohol (TBA), and 250 g water to form Solution C; mix Solution A and Solution B and agitate them uniformly at an ambient temperature to form a mixture solution; add Solution C to the mixture solution of Solution A and Solution B and agitate them for 3 minutes; use pressurized filtration to separate a solid from the solution; add the solid to a mixture solution containing 10 g polypropylene glycol (PPG) having a molecular weight of 400, 680 g tert-butyl alcohol (TBA), and 375 g water, and agitate them at an ambient temperature to disperse the solid uniformly in the solution; use pressurized filtration to separate the solid from the solution; add the solid to a mixture solution containing 5 g polypropylene glycol (PPG) having a molecular weight of 400 and 970 g tert-butyl alcohol (TBA), and agitate them at an ambient temperature to disperse the solid uniformly in the solution; use pressurized filtration to separate the solid from the solution; dry the solid in vacuum at a temperature of 60° C. to obtain the high-activity DMC catalyst.

Evaluation of the Catalyzing Activity of the Catalyst: Synthesizing Polyether Polyol Embodiment IV The method for fabricating polyoxypropylene diol having a molecular weight of 2000:

Add 750 g polypropylene glycol (PPG) as the starter compound (having a hydroxyl value=280 mg KOH/g) and 50 ppm (with respect to the total weight of products) catalyst to a pressure-resistant reactor, and heat the reactants to 120° C. under a nitrogen environment with persistent agitation; undertake the first stage of propylene oxide (PO) addition and add 225 g PO to the reactor; while the pressure of the reactor begins to decrease (it means that the catalyst has been activated), undertake the second stage of PO addition and add 2891 g PO to the reactor in a continuous feeding way; after the PO addition is completed, continuously agitate the reactants for 30 minutes at a temperature of 120° C.; let the reactor cool down to the ambient temperature; take out the product—polyether polyol for evaluation. The induction time of the catalyst is defined to be the time interval between the time point of the first stage of PO addition and the time point at which the pressure of the reactor begins to decrease. The activity of the catalyst is defined to be the amount of the propylene oxide catalyzed to be propoxylated by each gram of the catalyst each minute. The results are shown in Table. 1.

Embodiment V

The Method for Fabricating Polyoxypropylene Triol Having a Molecular Weight of 6000:

Embodiment V is essentially the same as Embodiment IV except the changes stated below: the starter compound is changed from 750 g polypropylene glycol (PPG) (having a hydroxyl value=280 mg KOH/g) to 650 g propoxylated glycerin (having a hydroxyl value=240 mg KOH/g); the amount of PO added in the first stage is changed to be 110 g; the amount of PO added in the second stage is changed to be 4875 g. The results are shown in Table 2.

Table 1 showing results of the reactions where catalysts catalyze the propoxylation of polypropylene glycol to generate polyether polypol ( 2K polyoxypropylene diol)

| | Catalyst features | 2K mw polyoxypropylene diol | | | | |
|---|---|---|---|---|---|---|
| Catalyst | Organic complexing ligand | Induction time (min) | Activity (kg PO/g Cat./min) | Viscosity (cps@25° C.) | Double-bond amount (meq/g) | Polydispersity Index (Mw/Mn) |
| E[a] I | EC 15 wt % + TBA | 14 | 228 | 319.4 | 0.007 | 1.03 |
| E II | EC 24 wt % + TBA | 111 | 197 | 359.2 | 0.004 | 1.04 |
| E III | EC 15 wt % + TBA + PPG | 2 | 294 | 295.4 | 0.007 | 1.03 |
| C[b] I | TBA | 25 | 17.2 | 333.3 | 0.004 | 1.04 |
| C II | PPG + TBA | 33 | 149 | 319.4 | 0.004 | 1.03 |

[a]Embodiment
[b]Comparison

Table 2 showing results of the reactions where catalysts catalyze the propoxylation of polypropylene glycol to generate polyether polypol ( 6K polyoxypropylene triol)

| | Catalyst features | 6K mw polyoxypropylene triol | | | | |
|---|---|---|---|---|---|---|
| Catalyst | Organic complexing ligand | Induction time (min) | Activity (kg PO/g Cat./min) | Viscosity (cps@25° C.) | Double-bond amount (meq/g) | polydispersity Index (Mw/Mn) |
| E[a] I | EC + TBA | 26 | 166 | 1184.1 | 0.001 | 1.07 |
| E III | EC + PPG + TBA | 14 | 130 | 1134.7 | 0.004 | 1.03 |
| C[b] I | TBA | 27 | 20 | 1190.2 | 0.006 | 1.06 |
| C II | PPG + TBA | 16 | 110 | 1131.8 | 0.002 | 1.05 |

[a]Embodiment
[b]Comparison

Figure 3:
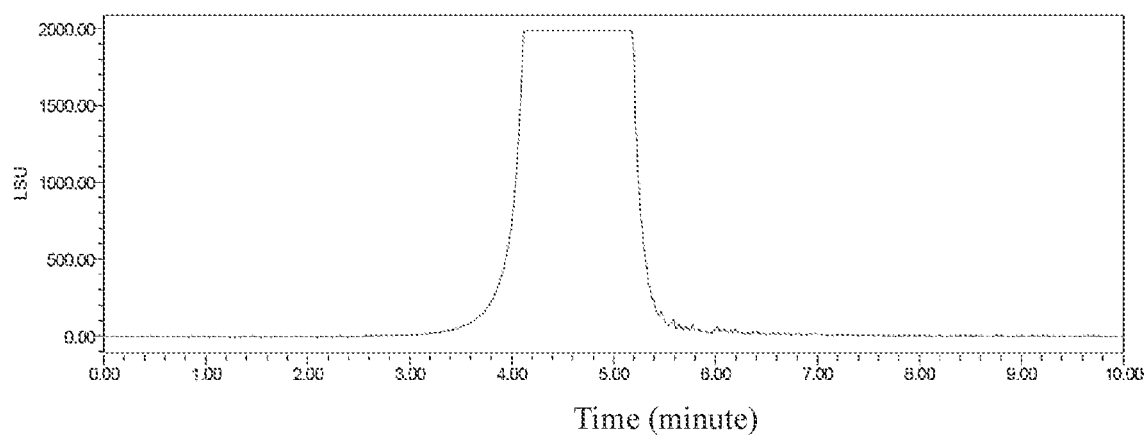
FIG. 3 is a diagram showing the GPC analysis spectrum of 6K polyoxypropylene triol, wherein the reactions for generating 6K polyoxypropylene triol uses the catalyst fabricated in Embodiment I.
Figure 4:
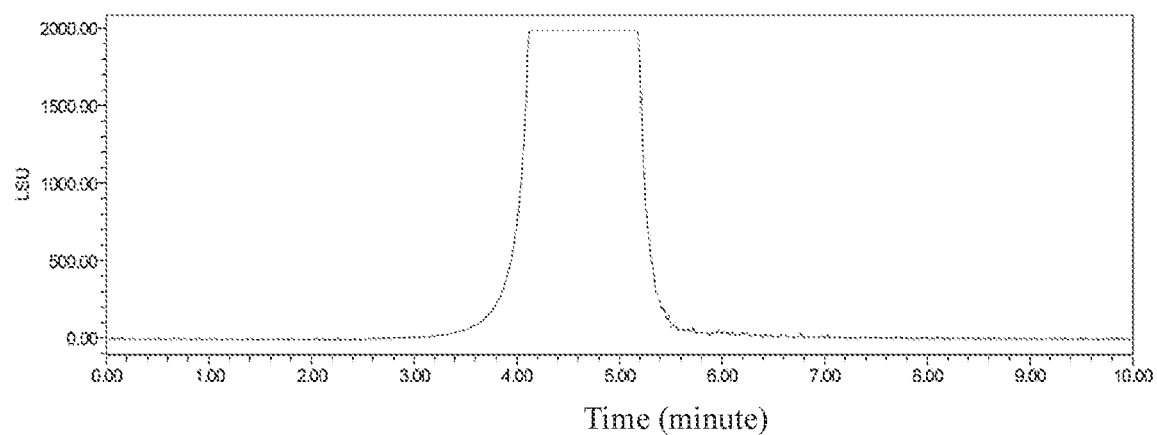
FIG. 4 is a diagram showing the GPC analysis spectrum of 6K polyoxypropylene triol, wherein the reactions for generating 6K polyoxypropylene triol uses the catalyst fabricated in Embodiment III.

Refer to FIG. 3 and FIG. 4 for the GPC analysis spectra of 6K polyoxypropylene triol, wherein the reactions for generating 6K polyoxypropylene triol respectively use the catalysts fabricated in Embodiment I and Embodiment III.

It is seen in the results of Embodiment I and Embodiment II (shown in Table 1): the method for fabricating high-activity DMC catalyst of the present invention can vary the amount of added ethylene carbonate to control the features of the catalyst and modify the characteristics of the polyol product.

It is seen in the results of Embodiment I and Embodiment III, Comparison I and Comparison II (shown in Table 1, Table 2, FIG. 3, and FIG. 4): the high-activity DMC catalyst of the present invention has higher catalyzing activity than the DMC catalysts of the conventional technologies, not only having a shorter catalyst induction time but also catalyzing the propoxylation of a higher amount of propylene oxide per unit time; the polyether polyols generated by the present invention has an insignificant amount of high-molecular-weight compounds for the concentration detection limit of 5 ppm and the molecular weight detection range of 1000-2000000.

Please refer to Table 1 and Table 2, in the test of the propylene oxide being polymerized to produce the polyether polyols, the required "induction time" in the early stage of the reaction can be greatly shorten by using DMC synthesized by adding EC as a catalyst. This clearly indicates that the added EC by the catalyst technology as disclosed above mainly has a significant effect on the high-activity DMC catalyst produced. Also, its catalytic "activity" has a significant correlation with the amount of the added EC.

In addition, please refer to the Table 3 below. It clearly shows that with the preparation of the catalyst, the increase in the amount of EC added as an organic complexing ligand does not have a significant effect on the polyether polyol produced by the propylene oxide polymerization using the high-activity DMC catalyst as the catalyst. There does not have any carbonate groups and ethyleneoxy groups in the structure of the polyether polyol, and there does not have much difference for the content of the Primary OH of the polyether polyol. This means that the added EC in the high-activity DMC catalyst synthesis method as disclosed by the present invention does not participate in any subsequent reactions using the high-activity DMC as a catalyst.

Table 3 Showing Results of the Reactions where Catalysts Catalyze the Propoxylation of Polypropylene Glycol to Generate Polyether Polyol (2K Polyoxypropylene Diol)

The function of adding the alicyclic carbonate when synthesizing the high-activity DMC catalyst in the present invention is to enhance the activity of the catalyst, not to participate in the subsequent catalytic reaction. The alicyclic carbonate only participates in the reaction when synthesizing the high-activity DMC catalyst. Therefore, the alicyclic carbonate will affect the activity of the high-activity DMC catalyst to make the high-activity DMC catalyst have the higher "Activity" (See Table 1 and Table 2) and the shorter "Induction time" (See Table 2) during the synthesis of the polyether polyols. The alicyclic carbonate does not participate in the reaction when subsequently used in the synthesis of polyether polyols. Therefore, the physical properties of the synthesized polyether polyols (such as Viscosity, Double-bond amount & Polydispersity Index) will not be significantly affected (See Table 1 and Table 2).

In conclusion, the present invention proposes a high-activity double-metal-cyanide catalyst, a method for fabricating the same, and applications of the same to fabricate polyols. The present invention can enhance the activity of the DMC catalyst via merely adding alicyclic carbonate to the conventional catalyst synthesis process. Further, the present invention can be used to generate polyols having less high-molecular-weight compounds. Therefore, the present invention is very useful in industry.

The embodiments described above are only to exemplify the present invention but not to limit the scope of the present invention. Any equivalent modification or variation according to the characteristic or spirit of the present invention is to be also included by the scope of the present invention.

What is claimed is:

1. A method for fabricating a high-activity double-metal-cyanide catalyst comprises:

mixing two metal precursor solutions to react in the presence of a fatty alcohol containing 2-7 carbon atoms and an alicyclic carbonate, to generate a resultant solution, wherein at least one of said two metal precursor solutions contains a cyanide ligand, wherein said resultant solution comprises a double-metal-cyanide compound and an organic complexing ligand including said fatty alcohol and said alicyclic carbonate, wherein said alicyclic carbonate coordinates with said double-metal-cyanide compound, wherein a concentration of said fatty alcohol in said organic complexing ligand is 2-98 mole %, and wherein said alicyclic carbonate has a structural formula expressed by chemical formula (I):

|  | Preparation of Catalyst: | Product: polyether polyol (Mw = 2000) | | |
|---|---|---|---|---|
|  | organic complexing ligand Content of organic complexing ligand | carbonate groups/molecule | Weight % ethylene oxy groups | Primary OH content % |
| C[b] I | EC 0 wt % + TBA | 0.0 | 0.0 | 8.9 |
| E[a] I | EC 15 wt % + TBA | 0.0 | 0.0 | 8.6 |
| E II | EC 24 wt % + TBA | 0.0 | 0.0 | 8.8 |

[a]Embodiment

[b]Comparison

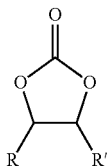 (I)

wherein R and R' are identical or different, and wherein each of R and R' is selected from a group consisting of hydrogen atoms, saturated alkyl groups each containing 1-20 carbon atoms, cyclic alkyl groups, hydroxyl groups, and vinyl groups;

flushing and filtering said resultant solution to remove excess organic complexing ligand from said resultant solution to make free alicyclic carbonate be absent; and separating said high-activity double-metal-cyanide catalyst without free alicyclic carbonate from said resultant solution.

2. The method for fabricating a high-activity double-metal-cyanide catalyst according to claim 1, wherein said fatty alcohol and said alicyclic carbonate exists in at least one of said two metal precursor solutions and mixes with a metal precursor; alternatively, said fatty alcohol and said alicyclic carbonate is added to said resultant solution immediately after said two metal precursor solutions are mixed.

3. The method for fabricating a high-activity double-metal-cyanide catalyst according to claim 2, further comprising mixing at least one functionalized compound with said two metal precursor solutions to react in the presence of said fatty alcohol and said alicyclic carbonate to generate a resultant solution, wherein said at least one functionalized compound is a compound containing at least one functional group, and wherein said at least one functional group is selected from a group consisting of oxygen, nitrogen, sulfur, phosphorus, and halogens.

4. The method for fabricating a high-activity double-metal-cyanide catalyst according to claim 3, wherein a concentration of said at least one functionalized compound in said high-activity double-metal-cyanide catalyst is 2-80 wt %.

5. The method for fabricating a high-activity double-metal-cyanide catalyst according to claim 4, wherein said at least one functionalized compound is selected from a group consisting of polyethers, polyesters, polycarbonates, polyalkylene glycol sorbitan esters, polyalkylene glycol glycidyl ethers, polyacrylamides, poly(acrylamide-co-acrylic acids), polyacrylic acids, poly(acrylic acid-co-maleic acid), poly(N-vinylpyrrolidone-co-acrylic acids), poly(acrylic acid-co-styrenes), salts of poly(acrylic acid-co-styrenes), maleic acids, styrenes and maleic anhydride copolymers, salts of styrenes and maleic anhydride copolymers, polyacrylonitriles, polyalkyl acrylates, polyalkyl methacrylates, polyvinyl methyl ethers, polyvinyl ethyl ethers, polyvinyl acetates, polyvinyl alcohols, poly-N-vinylpyrrolidones, polyvinyl methyl ketones, poly(4-vinylphenols), oxazoline polymers, polyalkyleneimines, hydroxyethylcelluloses, polyacetals, glycidyl ethers, glycosides, carboxylic acid esters of polyhydric alcohols, bile acids, salts, esters and amides of bile acids, cyclodextrins, phosphorus compounds, and unsaturated carboxylic acid esters.

6. The method for fabricating a high-activity double-metal-cyanide catalyst according to claim 2, wherein said two metal precursor solutions are mixed to react in an aqueous solution, and wherein said aqueous solution is at a temperature of 10-80° C.

7. The method for fabricating a high-activity double-metal-cyanide catalyst according to claim 1, wherein said two metal precursor solutions includes a metal salt and a metal cyanide salt, wherein said metal salt has a general formula expressed by chemical formula (II):

 (II)

wherein M in chemical formula (II) is selected from a group consisting of bivalent zinc (Zn(II)), bivalent iron (Fe (II)), bivalent nickel (Ni (II)), bivalent manganese (Mn (II)), bivalent cobalt (Co (II)), bivalent tin (Sn (II)), bivalent lead (Pb (II)), trivalent iron (Fe (III)), tetravalent molybdenum (Mo (IV)), hexavalent molybdenum (Mo (VI)), trivalent aluminum (Al (III)), pentavalent vanadium (V (V)), tetravalent vanadium (V (IV)), bivalent strontium (Sr (II)), tetravalent tungsten (W (IV)), hexavalent tungsten (W (VI)), bivalent copper (Cu (II)), and trivalent chromium (Cr (III)), and wherein X is selected from a group consisting of halogens, hydroxyl ion, sulfate ion, carbonate ion, cyanide ion, isocyanide ion, isothiocyanate ion, carboxylate ion, and nitrate ion, and wherein n equals 1-3 and charges in chemical formula (II) are in balance, and wherein said metal cyanide salt has a general formula expressed by chemical formula (III):

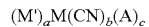 (III)

wherein M in chemical formula (III) is selected from a group consisting of bivalent iron (Fe (II)), trivalent iron (Fe (III)), bivalent cobalt (Co (II)), trivalent cobalt (Co (III)), bivalent chromium (Cr (II)), trivalent chromium (Cr (III)), bivalent manganese (Mn (II)), trivalent manganese (Mn (III)), trivalent iridium (Ir (III)), bivalent nickel (Ni (II)), trivalent rhodium (Rh (III)), bivalent ruthenium (Ru (II)), tetravalent vanadium (V (IV)), and pentavalent vanadium (V (V)), and wherein M' is selected from a group consisting of alkali metal ions and alkaline earth metal ions, and wherein A is an anion which is selected from a group consisting of halides, hydroxyl ion, sulfate ion, carbonate ion, cyanide ion, oxalate ion, thiocyanate isocyanide ion, isothiocyanate ion, carboxylate ion, and nitrate ion, and wherein each of a and b is an integer greater than 1, and wherein a sum of charges of groups subscripted by a, b and c is equal to a number of charges of M.

8. The method for fabricating a high-activity double-metal-cyanide catalyst according to claim 7, wherein M in chemical formula (II) is selected from a group consisting of bivalent zinc (Zn(II)), bivalent iron (Fe (II)) and bivalent cobalt (Co (II)), and wherein M in chemical formula (III) is selected from a group consisting of bivalent cobalt (Co (II)), trivalent cobalt (Co (III)), bivalent iron (Fe (II)), trivalent iron (Fe (III)), trivalent chromium (Cr (III)), trivalent iridium (Ir (III)) and bivalent nickel (Ni (II)).

9. The method for fabricating a high-activity double-metal-cyanide catalyst according to claim 7, wherein said metal salt is selected from a group consisting of zinc chloride, zinc sulfate, zinc bromide, zinc formate, zinc acetate, zinc propionate, zinc acetonylacetate, zinc benzoate, zinc nitrate, iron (II) sulfate, iron (II) bromide, cobalt (II) chloride, cobalt (II) thiocyanate, nickel (II) formate, and nickel (II) nitrate, and wherein said metal cyanide salt is selected from a group consisting of potassium hexacyanocobaltate (III), potassium hexacyanoferrate (II), potassium hexacyanoferrate (III), lithium hexacyanoiridate (III), lithium hexacyanocobaltate (III), sodium hexacyanocobaltate (III), calcium hexacyanocobaltate (III), and cesium hexacyanocobaltate (III).

10. The method for fabricating a high-activity double-metal-cyanide catalyst according to claim 7, wherein said double-metal-cyanide compound is selected from a group consisting of zinc hexacyanocobaltate (III), zinc hexacyanoferrate (II), zinc hexacyanoferrate (III), nickel (II) hexacyanoferrate (II), and cobalt (II) hexacyanocobaltate (III).

11. The method for fabricating a high-activity double-metal-cyanide catalyst according to claim 1, wherein said fatty alcohol is one or more compounds selected from a group consisting of ethanol, n-propyl alcohol, isopropyl alcohol, n-butanol, isobutyl alcohol, sec-butyl alcohol, tert-butyl alcohol, 2-methyl-3-buten-2-ol, and tert-amyl alcohol, and wherein said alicyclic carbonate is selected from a group consisting of ethylene carbonate, propylene carbonate, 1,2-butylene carbonate, pentylene carbonate, hexylene carbonate, octylene carbonate, dodecylene carbonate, glycerol carbonate, styrene carbonate, 3-phenyl propylene carbonate, cyclohexene carbonate, vinyl ethylene carbonate, 4, 4-dimethyl-5-methylene-(1, 3) dioxolan-2-one, and 4-allyl-4, 5-dimethyl-5-(10-undecenyl)-1, 3-dioxolan-2-one.

12. The method for fabricating a high-activity double-metal-cyanide catalyst according to claim 1, wherein a concentration of said alicyclic carbonate in said organic complexing ligand ranges from 2 to 98 mole %.

* * * * *